United States Patent
De Sisternes et al.

(10) Patent No.: US 11,998,272 B2
(45) Date of Patent: Jun. 4, 2024

(54) POST-PROCESSING METHOD TO IMPROVE LSO-BASED TRACKING IN OCT

(71) Applicants: Carl Zeiss Meditec, Inc., Dublin, CA (US); Carl Zeiss Meditec AG, Jena (DE)

(72) Inventors: Luis De Sisternes, San Francisco, CA (US); Patrick Krawec, Lafayette, CA (US); Simon Bello, Walnut Creek, CA (US); Sophie Kubach, Menlo Park, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 734 days.

(21) Appl. No.: 16/967,679

(22) PCT Filed: Apr. 15, 2019

(86) PCT No.: PCT/EP2019/059716
§ 371 (c)(1),
(2) Date: Aug. 5, 2020

(87) PCT Pub. No.: WO2019/201881
PCT Pub. Date: Oct. 24, 2019

(65) Prior Publication Data
US 2021/0030269 A1    Feb. 4, 2021

Related U.S. Application Data

(60) Provisional application No. 62/659,538, filed on Apr. 18, 2018.

(51) Int. Cl.
*A61B 3/10*    (2006.01)
*A61B 3/00*    (2006.01)
(Continued)

(52) U.S. Cl.
CPC ............ *A61B 3/102* (2013.01); *A61B 3/0025* (2013.01); *A61B 3/13* (2013.01); *G06T 5/00* (2013.01);
(Continued)

(58) Field of Classification Search
CPC ..... A61B 3/102; A61B 3/0025; A61B 3/1225; A61B 3/14; A61B 3/1005;
(Continued)

(56) References Cited

U.S. PATENT DOCUMENTS

| 4,144,569 A | 3/1979 | Wagner |
| 5,321,501 A | 6/1994 | Swanson et al. |

(Continued)

FOREIGN PATENT DOCUMENTS

| JP | 2011508241 | 3/2011 |
| JP | 2011188946 | 9/2011 |

(Continued)

OTHER PUBLICATIONS

International Search Report and Written Opinion for International Patent Application No. PCT/EP2019/059716 dated Jul. 23, 2019, 10 pages.

(Continued)

*Primary Examiner* — Brandi N Thomas
(74) *Attorney, Agent, or Firm* — Snell & Wilmer L.L.P.

(57) ABSTRACT

After OCT scans are acquired, error compensation is be applied anew by identifying motion tracking data that was collected simultaneously with (or closest in time to) each acquired OCT scan. The effects of any previously applied motion tracking information is removed from an OCT scan before applying the new motion tracking data, which may provide higher resolution motion tracking.

21 Claims, 11 Drawing Sheets

(51) Int. Cl.
*A61B 3/13* (2006.01)
*G06T 5/00* (2006.01)
(52) U.S. Cl.
CPC ............ *G06T 2207/10101* (2013.01); *G06T 2207/30041* (2013.01)
(58) Field of Classification Search
CPC .... A61B 2560/0431; A61B 2562/0214; A61B 2562/0257; A61B 2562/223; A61B 3/0008; A61B 3/10; A61B 3/13; A61B 3/132; A61B 3/0058; A61B 3/107; A61B 3/12; A61B 3/152; A61B 3/0075; A61B 3/15; A61B 3/103; A61B 3/18; A61B 3/0041; A61B 3/0091; A61B 5/0066; A61B 5/6821; A61B 5/026; A61B 5/0285; A61N 2005/1091; A61N 5/1017; A61N 2005/1059; A61N 2005/1072; A61N 5/1049; A61N 5/1067; A61N 5/103; A61N 5/1037; A61N 5/1064; G01B 9/02007; G01B 2290/25; G01B 2290/45; G01B 2290/60; G01B 9/02004; G01B 9/02029; G01B 9/02049; G01B 9/0207; G01B 9/02077; G01B 9/02083; A61F 2009/00844; A61F 2009/00863; A61F 9/008
See application file for complete search history.

(56) References Cited

U.S. PATENT DOCUMENTS

| | | | |
|---|---|---|---|
| 7,768,652 | B2 | 8/2010 | Everett |
| 7,805,009 | B2 | 9/2010 | Everett et al. |
| 8,857,988 | B2 | 10/2014 | Sharma et al. |
| 8,938,280 | B2 | 1/2015 | Harvey |
| 9,269,144 | B2 | 2/2016 | Kraus et al. |
| 9,706,915 | B2 | 7/2017 | Everett et al. |
| 2006/0228011 | A1* | 10/2006 | Everett .............. A61B 3/102 382/128 |
| 2007/0291277 | A1 | 12/2007 | Everett et al. |
| 2011/0267340 | A1 | 11/2011 | Kraus et al. |
| 2012/0249956 | A1 | 10/2012 | Narasimha-Iyer et al. |
| 2013/0176532 | A1 | 7/2013 | Sharma et al. |
| 2015/0294147 | A1 | 10/2015 | Wisweh |
| 2015/0313466 | A1 | 11/2015 | Yoshida |

FOREIGN PATENT DOCUMENTS

| | | |
|---|---|---|
| JP | 2011212213 | 10/2011 |
| JP | 2013202298 | 10/2013 |
| JP | 2014509544 | 5/2015 |
| JP | 2016508799 | 3/2016 |
| JP | 2016047076 | 4/2016 |
| WO | 2010062860 | 6/2010 |
| WO | 2012130976 | 10/2012 |
| WO | 2014191031 | 12/2014 |

OTHER PUBLICATIONS

Kraus et al., (2012). "Motion correction in optical coherence tomography volumes on a per A-scan basis using orthogonal scan patterns," Biomed. Opt. Express, 3:1182-1199.
Lang et al., (2016). "Combined registration and motion correction of longitudinal retinal OCT data," Proceedings SPIE International Society for Optical Engineering, 9784:97840X, 15 pages.
Wikipedia, (2001). "Delaunay triangulation process," available online at <en.wikipedia.org/wiki/Delaunay_triangulation>, 7 pages.
China National Intellectual Property Office, First Office Action dated Sep. 28, 2023 in CN Serial No. 201980009358.1.
China National Intellectual Property Office, Search Report dated Sep. 27, 2023 in JP Serial No. 2019800093581.
Japan Patent Office, Notice of Reasons for Refusal dated Jan. 19, 2023 In JP Serial No. 2020-539795.

* cited by examiner

POST-PROCESSING METHOD TO IMPROVE LSO-BASED TRACKING IN OCT

PRIORITY

This application is a National Phase application under 35 U.S.C. § 371 of International Application No. PCT/EP2019/059716, filed Apr. 15, 2019, which claims priority to U.S. Provisional Application Ser. No. 62/659,538, filed Apr. 18, 2018, the contents of which are hereby incorporated by reference in their entirety.

FIELD OF INVENTION

The present invention is generally directed to the field of optical coherence tomography (OCT) and OCT angiography (OCTA). More specifically, it is directed to reducing artifacts due to motion tracking errors, particularly as manifested in enface images.

BACKGROUND

An optical coherence tomography (OCT) system may include an image camera to track motion of a subject being examined, and an OCT scanner to scan the subject. The image camera may be used to provide motion tracking information to the OCT scanner, which may use the motion information to guide and/or correct a scanning operation. Error in motion tracking can therefore have a direct effect on the quality of OCT scans.

Work has been proposed to correct for motion in OCT scans both during acquisition of OCT data (e.g., an OCT scan) and as a post-processing technique. An LSO-based tracking algorithm has been presented which uses LSO images acquired at the same time as the OCT data to guide the location of an OCT scanner for acquisition and to decide if a particular OCT frame needs to be re-scanned (see for example, U.S. Pat. No. 8,857,988). Other algorithms may rely in the acquisition of several repeated OCT datasets. U.S. Pat. No. 9,706,915 describes a method in which a first acquisition of OCT data is done in a reduced number of locations so that the data can be considered substantially stationary and a second acquisition, with more data locations, can be registered to it. However, acquiring stationary data is extremely difficult since eye movements can be very fast and unpredictable. Other methods use the acquisition of two orthogonal three-dimensional datasets to correct for motion retrospectively using image registration algorithms on the OCT datasets themselves. Additional methods rely on the segmentation of blood vessels in OCT images and a regularization algorithm to correct for the motion (see for example, Lang A. et al., "Combined registration and motion correction of longitudinal retinal OCT data", *Proceedings of SPIE—The International Society for Optical Engineering*, 2016; 9784:97840 X). However, the results from these methods may be dependent in the performance of the segmentation methods used in individual steps of the algorithm.

Although mostly successful, current methods to correct for motion in OCT images have several limitations, including: (1) Acquiring repeated OCT data in several acquisitions at different directions is time-consuming and may require the acquisition of data in a substantially stationary position; (2) The result from acquiring repeated data at multiple directions to correct for motion may also come at the expense of loss or blurring of fine details; and (3) The use of intermediate segmentation steps may result in failure cases.

It is an object of the present invention to provide a method/device/system for improved motion correction in OCT and OCTA images.

It is a further object of the present invention to provide motion correction irrespective of the motion tracking algorithm used.

SUMMARY OF INVENTION

The above objects are met in an OCT, or OCTA, system or method that uses an imaging camera (e.g., a line scan ophthalmoscope, LSO) for motion tracking, and an OCT scanner that uses the tracking information for OCT scan guidance. The present invention overcomes the main limitations in motion correction for OCT systems that use LSO tracking data (or other types of motion tracking data) to guide OCT acquisition. The present invention is applied retrospectively to already acquired data using the information collected during acquisition, so it is not subject to the restrictive execution time limitations during acquisition and at the same time can correct for motion using "real-time" motion tracking transformations instead of "near real-time" motion tracking transformations. That is, after all OCT and motion tracking associated data is acquired, any errors made during motion tracking may be corrected by inverting (e.g., undoing) the effect of the motion tracking transformations that had been commanded to (e.g., used by) the OCT camera (e.g., OCT photodetector) for each frame (e.g., OCT scan acquisition) and applying an effect of corrected (e.g., more closely matched) observed tracking transformation to each frame.

The present invention may correct motion errors in a whole OCT or OCT angiography (OCTA) volume without a need for repeated acquisitions of the volume (either in a sparse manner or by two orthogonal directions).

The present invention may be implemented in a method or system for motion correction in optical coherence tomography data. The method or system may include collecting motion-tracking data, where each collected motion-tracking datum has a respective motion-tracking time stamp, or other sequence indicator that permits determination of when two (or more) events occur relative to each other, such as in time relative to each other or in absolute time. For example, if a motion tracking datum includes a fundus image among multiple, sequentially captured, fundus images, then the motion tracking indicator may indicate the sequence in which its fundus image was captured within the sequentially captured fundus images. It is to be understood that gaps may exist in such a sequence if not all captured fundus images provide useful motion tracking data. Concurrent with the collecting of motion-tracking data, an OCT scanner may acquire multiple OCT scans, where each acquired OCT scan may have a respective OCT scan time stamp, or other sequence indicator that may permit comparing a relative time difference between when a motion-tracking datum is collected and an OCT scan is acquired. For example, an OCT scan sequence indicator may indicate the order in which useful OCT scans are acquired. It is to be understood that gaps may exist in such a sequence if some OCT scans are discarded as bad. In such a case, the OCT system may need to go back and try again when time permits, e.g., interrupt a current scan sweep and return to the missed location on a sample. Consequently, the OCT scan sequence indicator might not correspond to a sequential scan sweep of locations on a sample. The acquired OCT scans may then be matched to collected motion-tracking data based on their respective OCT time stamps and motion-tracking time stamps. For example, the acquired OCT scans may be matched to the collected motion-tracking data with most closely matching time stamps. Displacement error in the acquired OCT scans may then be corrected based on their matched collected motion-tracking data, and the displacement-corrected OCT scans may be displayed or stored for future analysis.

It is noted that typically, the acquisition of an OCT scan is guided by a previously collected motion-tracking datum, but the matched collected motion-tracking data may not be the same as that used for OCT scan acquisition. Therefore, applying motion correction to the already acquired OCT scans based on their matched collected motion-tracking data may cause their corresponding A-scans shift irregularly from their original regular positions. Therefore, the correcting for displacement error in the acquired OCT scans based on their matched motion-tracking data may include steps for compensating for this irregularity of shifted A-scans. For example, the corrected locations of A-scans in the OCT scans based on their matched motion correction data may be determined, and these corrected locations may constitute a point cloud of irregular point locations. The point cloud may then be transformed into a uniform coordinate grid with A-scans at regularly ordered positions within the grid.

For example, the point cloud may be transformed into a uniform coordinate grid by interpolating new A-scans at the regularly ordered positions based on the A-scans at irregular point locations within the point cloud. An approach towards doing this may include interpolating the new A-scan based on a set of three A-scans within the point cloud whose locations define a triangle of smallest area around the regularly ordered position.

Alternatively, a new A-scan may be interpolated at a regularly ordered position by triangulating the point cloud so that each A-scan location in the point cloud corresponds to a vertex in a set of triangles. Each regularly ordered position within the coordinate grid may then be associated to a corresponding set of three locations in the point cloud. In this manner, each corresponding set of three locations may define the vertexes of a triangle that includes the associated regularly ordered position within the coordinate grid. A look-up-table (LUT) having an entry for each ordered position within the coordinate grid may then be generated. Each entry in the LUT may include the ordered position's corresponding set of three locations in the point cloud and weights based on Barycentric coordinates of the ordered position's with respect to its associated triangle. New A-scans may then be interpolated based on the LUT.

In a case where the motion-tracking data includes multiple, individual motion-tracking data, and each individual motion-tracking datum includes an image and a first tracking transformation of first resolution based on the image, the present invention may further include, for each individual motion-tracking datum, creating a second tracking transformation of second resolution higher than the first tracking transformation. The displacement error in the acquired OCT scans may then be corrected based on the respective second tracking transformation of their matched motion-tracking data.

In embodiments, each OCT scan may be associated with a corresponding motion-tracking datum, and each OCT scan applies first motion compensation based on its associated motion-tracking datum. In this case, the step of correcting for displacement error in the acquired OCT scans based on their matched motion-tracking data may include applying second motion compensation to the acquired OCT scans base on their respectively matched collected motion-tracking data. Again, it is noted that the matched collected motion tracking datum of an OCT scan may be different than the associated corresponding motion-tracking datum. Furthermore, the application of first motion compensation to an OCT scan based on its associated motion-tracking datum may include using the associated motion-tracking datum to guide the acquisition of the OCT scan.

Additionally, each motion-tracking datum may include an image and a first tracking transformation based on the image, and each OCT scan may further be associated with the image of its associated motion-tracking datum. In this case, the step of applying second motion compensation to the acquired OCT scans base on their respectively matched collected motion-tracking data, may include: disassociating the image of its associated motion-tracking datum; associating the image of its matched collected motion-tracking datum; and generating the second motion compensation based on the image of its matched collected motion-tracking datum.

Furthermore, the first motion compensation may be generated based on the image of its associated motion-tracking datum, and a resolution of the image of its associated motion-tracking datum may be lower than a resolution of the image of its matched collected motion-tracking datum. For example, the image of its matched collected motion-tracking datum may be up-sampled to achieve a resolution higher than the image of its associated motion-tracking datum, if necessary.

In embodiments, each acquired OCT scan may be matched to the collected motion-tracking datum whose motion-tracking time stamp is closest to its OCT time stamp. Also, an LSO may be used to collect motion-tracking data. As stated above, the present method or system may be implemented an OCTA. For example, the acquired OCT scans may provide OCT angiography data.

If each motion-tracking datum has a motion-tracking sequence indicator instead of a motion-tracking time stamp, and each OCT scan has an OCT scan sequence indicator instead of a OCT scan time stamp, then the step of matching acquired OCT scans to collected motion-tracking data based on their respective OCT scan sequence indicator and motion-tracking sequence indicator may be done differently. In this approach, each OCT scan already has an existing association with a collected motion-tracking datum. For example, each OCT scan may be associated with the motion-tracking datum originally used to guide its scan acquisition (e.g., associated with a preliminary motion tracking datum). For a target OCT scan whose displacement error is to be corrected, one identifies its associated preliminary motion-tracking datum. Then, starting from the identified preliminary motion-tracking datum, one may shift along the collected motion-tracking data according to their motion-tracking sequence indicators by a predefined offset to reach a target motion-tracking datum. This predefined offset may be a "one" position offset. The target OCT scan is then matched the target motion-tracking datum. Alternatively if the motion-tracking datum is a motion-tracking time stamp, then the offset may be based on a difference between the motion-tracking time stamp of the identified preliminary motion-tracking datum and the OCT scan time stamp of the target OCT scan.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Embodiments according to the invention are disclosed in the attached claims directed to a method, a storage medium, a system, a device and/or a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts.

DESCRIPTION OF THE PREFERRED EMBODIMENTS

Figure 1:
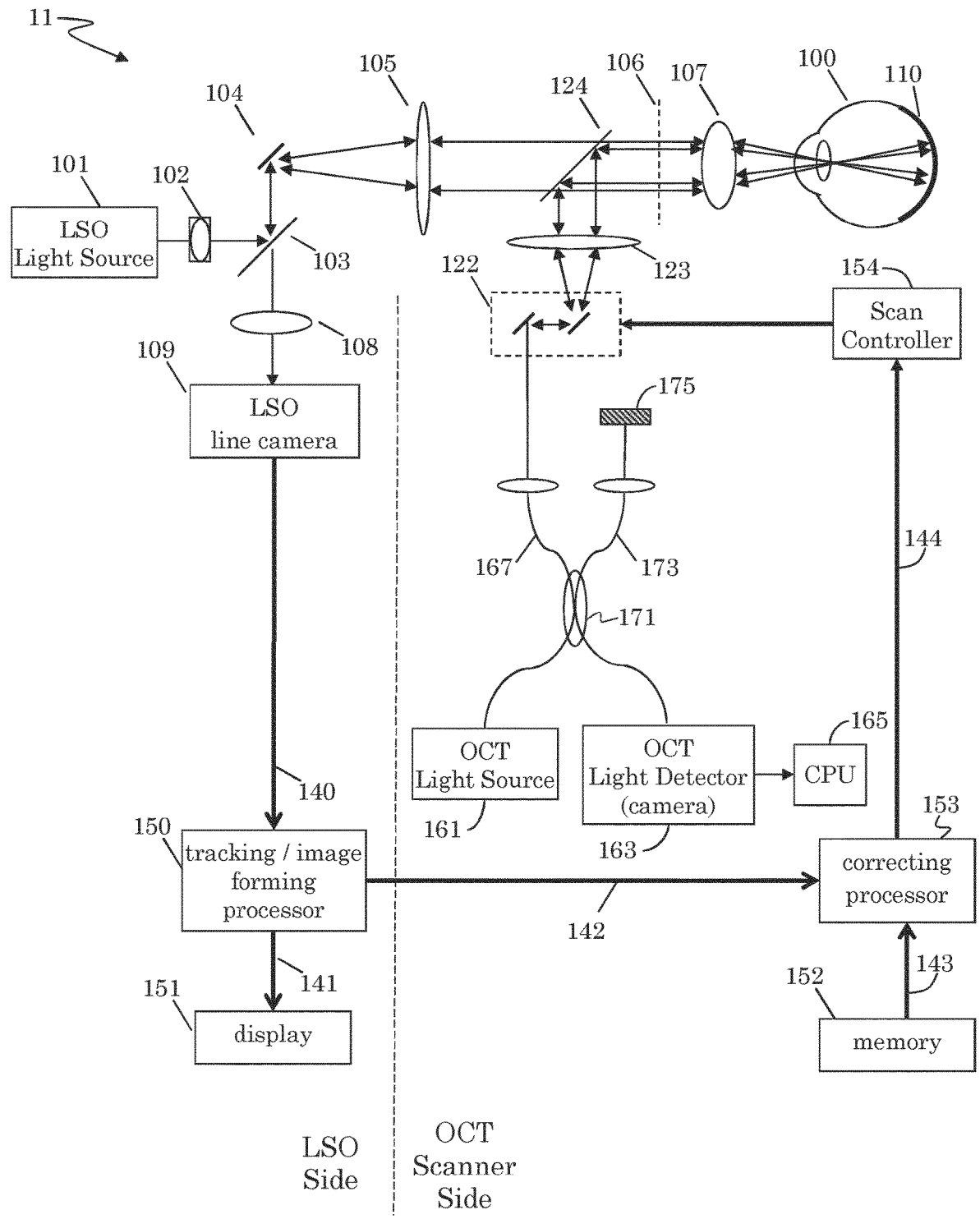
FIG. 1 illustration a simplified OCT system incorporating eye tracking based on a line-scan ophthalmoscope (LSO) and OCT scanner, symbolically separated by a dotted line for ease of discussion.

It is noted that in an optical coherence tomography (OCT) system that uses motion tracking to guide the acquisition of OCT scans (e.g., B-scan or frames), the motion tracking information used to guide a current OCT scan acquisition step is generated using sensor data (e.g., image data) gathered prior to the current OCT scan acquisition step. Typically, the motion tracking information is acquired in as "near real-time" as practical, but there is an inherent delay between the generation of the motion tracking information and the acquisition of the OCT scan based on the generated motion tracking information. Thus, the motion information used to guide an OCT scan is not "real time" information, and may not be able to account for current displacement error. An approach toward alleviating this difficulty is to speed up the generation of motion tracking information to be "near real time," as close to real time as practical. This typically entails down sampling the sensor data (e.g., image data) used for motion tracking, but this results in motion tracking information of lower resolution, which may itself introduce error. It would be beneficial to use high resolution sensor data and sophisticated motion tracking algorithms, but both of these approaches would introduce a delay to the acquisition of an OCT scan.

The present invention addresses these difficulties by application of post processing. Firstly, all (or a substantial amount) of captured sensor data (e.g., images), generated motion tracking information, and acquired OCT scans may be collected (stored). Error compensation may then be applied anew to the already acquired OCT scans by identifying (i.e. matching) the sensor data that was collected simultaneously with (or closest in time to) each acquired OCT scan. Each OCT scan would have already received first motion compensation based on its associated sensor data. The effect(s) of this first motion compensation may be removed from each acquired OCT scan, and the OCT scan may be associated with its matching sensor data. Second motion compensation may then be generated using its matched sensor data, and this second motion compensation may then be applied to the acquired OCT scan. It is noted that since this second motion compensation is generated after the OCT scan is already acquired, the second motion compensation may use higher resolution sensor data and/or more sophisticated motion tracking algorithms without affecting the OCT scan acquisition sequence. Consequently, this process may be applied to libraries of previously acquired OCT scans provided that sufficient, original sensor data for the OCT scans was also stored.

The present invention may be applied to any OCT system using tracking information to guide OCT scans, but for the sake of simplicity, particular examples discussed below may be directed to an OCT system having a fundus imager (particularly a line scan ophthalmoscope, LSO) and to an OCTA system, such as those used to examine an eye. Unless otherwise specified, the term "OCT scan" may refer to an OCT B-scan, or "fast scan." It is to be understood, however, that when one applies displacement error correction to a B-scan, or applies motion compensation to the acquisition of a B-scan, one is inherently applying displacement error correction or motion compensation to A-scans since a B-scan is comprised of a multiple A-scans.

FIG. 1 illustration a simplified OCT system 11 incorporating eye tracking based on a line-scan ophthalmoscope (LSO) and OCT scanner, symbolically separated by a dotted line for ease of discussion. It is to be understood, however, that the OCT scanner side of the dotted line incorporates many more components integral to an OCT system than a scanner 122, and the LSO and OCT may share multiple components in common. In the present example, light from an LSO light source 101 may be routed by lens 102 (e.g., a cylindrical lens, which focuses light into a line instead of a point) and beamsplitter 103 to scanning mirror 104. The cylindrical lens 102 and the scan lens 105 may produce a line of illumination at a retinal image plane 106, and an ocular lens 107 and optics of an eye 100 may re-image this line of illumination onto the retina 110. The line of illumination may be swept across the retina 110 as the scanning mirror 104 rotates. Reflected light from the retina approximately reverses the path of the LSO illumination light, e.g., the reflected light is de-scanned by the LSO scan mirror 104 so that the illuminated portion of the retina is stationary and imaged by imaging lens 108 onto an LSO line camera 109. The LSO line camera may convert the reflected LSO light into a data stream 140 representing single-line of partial images (e.g., line images), which may be processed by one or more processor 150 to form a full-frame image. Processor 150 may produce both eye tracking information for the OCT scanner side (conveyed along data path 142), and a full-frame image of the retina, e.g., a fundus image, for viewing on display 154 (conveyed along data path 141).

On the OCT scanner side, light from light source 161 is conveyed via fiber coupler 171, along optical fiber 167, to illuminate the sample (e.g., fundus 110). The light source 161 may be, for example, a broadband light source with short temporal coherence length in the case of spectral domain OCT (SD-OCT) or a wavelength tunable laser source in the case of swept source OCT (SS-OCT). Scanner 122 scans the light from source 161 so that the beam of light is scanned (e.g., laterally) over the area or volume to be imaged. Backscattered light returning from the sample (e.g., eye 100) is descaned by scanner 122 and is collected, typically into the same fiber 167 used to rout the light for illumination. Reference light derived from the same OCT light source 161 travels a separate path, in this case involving fiber 173 and retro-reflector 175 with an adjustable optical delay. As it is known in the art, a transmissive reference path can also be used and that the adjustable delay could be placed in the sample or reference arm of the interferometer. Collected sample light is combined with reference light, typically in a fiber coupler 171, to form light interference in a detector 163 (or collector of camera). Although a single fiber port is shown going to the detector 163, those skilled in the art will recognize that various designs of interferometers can be used for balanced or unbalanced detection of the interference signal. The output from the detector 163 is supplied to one or more processors 165, which may determine a depth profile of backscattered light. It is to be understood that processor 165 (or its functionality) may be incorporated into processor 150, and vice versa. Each line of data in the axial, or depth, direction (z-direction) is called an A-scan. A cross-sectional tomograph, or B-scan, can be obtained by combining a series of A-scans (e.g. laterally). A variety of ways to create B-scans are known, including but not limited to, along the horizontal or x-direction, along the vertical or y-direction, along the diagonal of x and y, or in a circular or spiral pattern. For example, a collection of adjacent B-scans may constitute a volume, or block, of OCT data. Typically, the direction of A-scan collection that defines one B-scan may be termed the fast scan direction, and the direction of obtaining multiple adjacent B-scans to define a volume may be termed the slow scan direction. The OCT scanner side may use time or frequency domain methods (spectral domain, swept-source, etc., see for example U.S. Pat. No. 5,321,501 and US Publication No. 2007/0291277 hereby incorporated in their entirety by reference). The sample and reference arms in the interferometer may consist of bulk-optics, fiber-optics or hybrid bulk-optic systems and could have different architectures such as Michelson, Mach-Zehnder or common-path based designs, as is known in the art. Light beam as used herein may be interpreted as any carefully directed light path. In time-domain systems, the reference arm may have a tunable optical delay to generate interference. Balanced detection systems may typically be used in time domain OCT (TD-OCT) and SS-OCT systems, while spectrometers may typically be used at the detection port for SD-OCT systems. The present invention may be applied to any type of OCT system using motion tracking and capable of generating data for structural OCT and/or for OCTA angiography analysis, including spot scanning, multi-spot scanning, partial field and full field imaging systems. The techniques described herein could be applicable to any body parts, for example eye (both anterior and posterior chambers), skin, brain, muscle, cochlear, and internal organs if integrated with endoscope or catheter probe. OCT scanner 122 may sweep the angle of the OCT beam (from OCT light source 161) in two dimensions, under control of a scan controller 154. Scan lens 123 may bring the OCT beam into focus on the retinal image 106. Beamsplitter 124 may combines the OCT and LSO beam paths so that both paths can more easily be directed through the pupil of the eye 100, e.g., a human eye. (Combining the beam paths may not be required in direct imaging applications, where the object itself lies in the location of retinal image 106.) If the OCT and LSO use different wavelengths of light, beamsplitter 124 may be implemented as a dichroic mirror. The OCT beam may be re-focused onto the retina 110 through ocular lens 107 and the optics of eye 100.

In the present example, the LSO may be used to track motion of the eye. In this manner, the positioning commands sent to the scanner may be adjusted so that the scan beam reaches the desired positions on the subject (e.g., a specific location on the retina 110). It is therefore desirable that information on the motion of the subject be provided with low latency so that the OCT scanning beam may be correctly positioned for each A-scan. Various methods of motion tracking are known, but most compare a current captured image to a reference image. For example, processor 150 may construct a full frame image to be used as the reference image. This may be the first good image captured in a sequence. A predefined number of easily identifiable characteristic features (e.g., large vessels, vessel crossings, high contrast areas, etc.) may be identified, mapped, and cataloged. As each new full-frame image (e.g., a fundus image) is captured/constructed, processor 150 attempts to extracts the same characteristic features and compare their positions relative to those of the reference image. If this operation fails, the current fundus image may be discarded. If the current image and reference image are successfully aligned, a motion transformation may be constructed, or example, by determining the translational and rotational displacement needed to align the characteristic features of both images. The motion transformation (or the displacement information) may be passed to correcting processor 153, which may combine it with a set of locations (e.g., a galvo table) 143 that specifies where an OCT scan should be acquired. This may become part of a commanded scan instruction, which the scan controller 154 may use to control scanner 122 to direct the OCT beam to the desired location on the eye.

Figure 2:
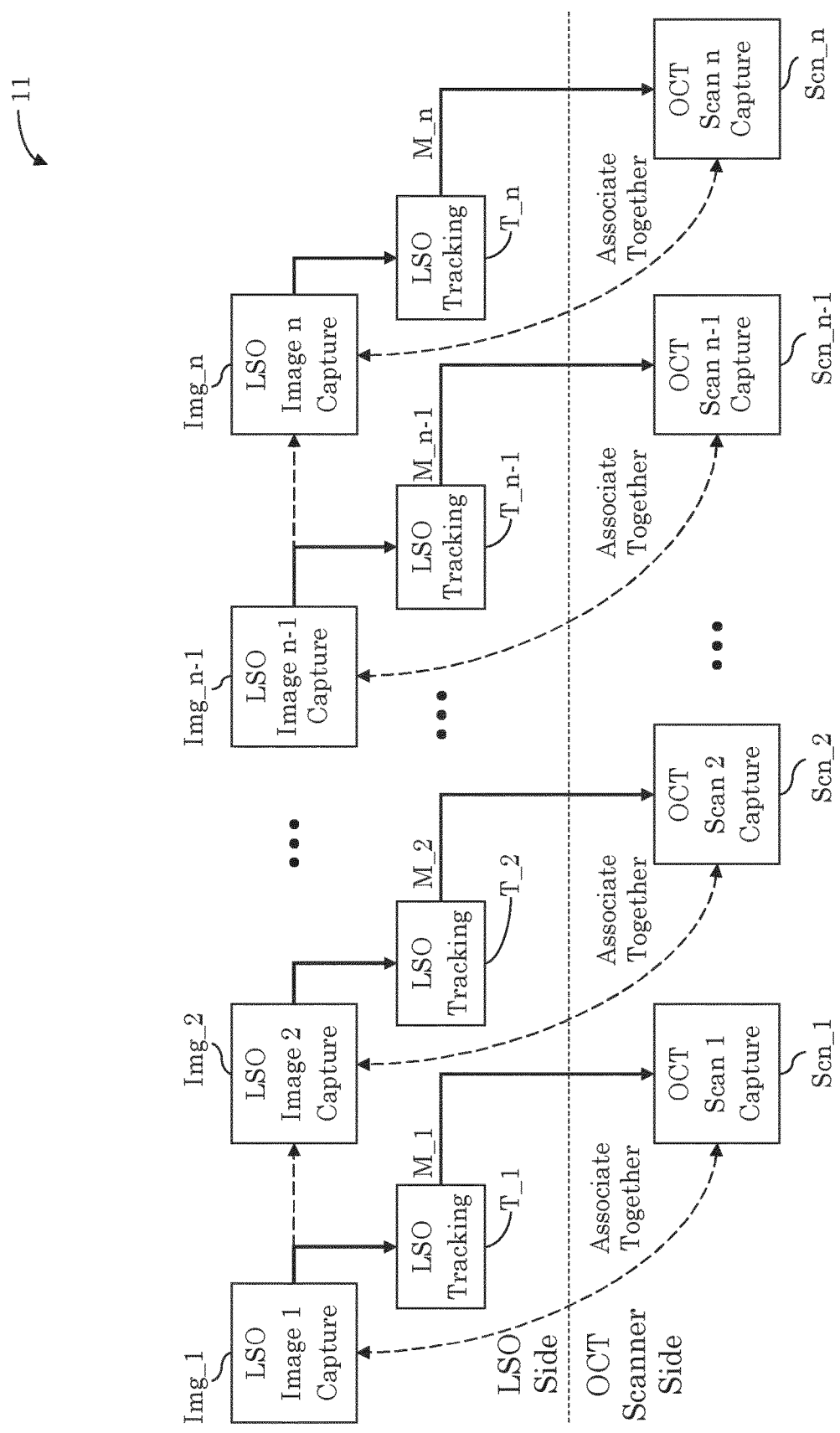
FIG. 2 illustrates an operational view of a typical optical coherence tomography (OCT) system, which may include a line scan ophthalmoscope (LSO) and an OCT scanner.

FIG. 2 illustrates an operational view of the typical optical coherence tomography (OCT) system 11 which may include a line scan ophthalmoscope (LSO) and an OCT scanner, such as that illustrated in FIG. 1. The LSO may acquire fundus images to track motion of the eye over time. As is explained above, the LSO may function concurrently with the OCT scanner. A continuous stream of LSO images (e.g., full or partial fundus images) Img_1 to Img_n may be used as the input to a tracking algorithm (e.g., T_1 to T_n) along with a "reference" image (not shown) to which a current image may be compared to detect relative displacement. This displacement information, which may be encapsulated in a motion or displacement transformation, (M_1 to M_n) is passed to the OCT, which uses it generate/acquire one or more OCT scans per LSO image (Scn_1 to Scn_n). Each acquired OCT scan is associated with the LSO image from which the displacement information used to acquire it is generated. For example, the one or more OCT scans Scn_1 are acquired by use of (preliminary) displacement information M_1, which is generated from LSO image Img_1, so the one or more OCT scans Scn_1 are associated with (preliminary) LSO image Img_1. It is noted that although the OCT typically sweeps across a subject in sequence (e.g. a sweep may be a sequence of B-scans scanning from top to bottom across a sample), the OCT scans of Scn_1 to Scn_n might not correspond to a continuous sweep across the subject. For example, if an OCT scan fails at a first sweep location while the one or more OCT scans of scn_1 are being acquired, the OCT will return to that failed sweep location at a later time. It may happen that by the time the OCT returns and successfully scans the previously failed sweep location, that successful scan may be part of Scn_2 or some later scan capture sequence. Thus the OCT scans of a single sweep may be intermixed among multiple OCT scan capture sequences (Scn_1 to Scn_n).

The motion information (e.g., M_1 to M_n) extracted from the LSO images (e.g., Img_1 to Img_n) can be detected and passed to the OCT scanner in near real-time, which may use the received (preliminary) motion information to apply motion correction to the generated (e.g., acquired) OCT scans (e.g., Scn_1 to Scn_n). However, since this information cannot be generated and passed in absolute real-time, there is an inherent limitation of possible small movements between the detected motion that was passed to the OCT scanner and newly detected motion at the time the scan is collected. For example, LSO image Img_1 may be passed to the tracking algorithm, which extracts motion information M_1. This motion information M_1 may be passed to the OCT scanner, which uses the information to guide the acquisition of an OCT scan (Scn_1), and associates (at least preliminarily) the acquired OCT scan (Scn_1) with the SLO image (Img_1) corresponding to the received motion correction information (M_1). However, by the time OCT scan Scn_1 is generated/acquired, another LSO image (e.g., Img_2) may be have been taken, whose motion information (e.g., M_2) may be more current to Scn_1. This limitation, together with the fact that there is also a limitation in the precision of the tracking algorithm imposed by the need for near real-time execution, constitutes a trade-off: Faster algorithm speeds result in tracking closer to real-time and hence less possible movements between extracted motion information and corresponding OCT scan generation, but faster motion tracking generally uses a tracking algorithm of less precision.

The present invention may make use of motion-tracking sequence indicators to track motion-tracking data, which may include an LSO image and/or its extracted motion/ displacement information or transformation. The present invention may also make use of OCT scan sequence indicators to keep track of OCT scans. For example, motion-tracking sequence indicators may be identifiers Img_1 to Img_n, which identify successfully captured LSO images in sequence and/or may be a time stamp indicating when an LSO image was successfully captured. Similarly, OCT scan sequence indicators may be identifiers Scn_1 to Scn_2, which identify successful OCT scan sequences and/or may be a time stamp indicating when an OCT scan was successfully acquired. An object of the present invention is to match each OCT scan sequence (Scn_1 to Scn_n) to an LSO image (Img_1 to Img_2) that was captured at substantially the same time as when the OCT scan sequence was acquired, and to update the OCT scan sequence's displacement correction based on the matched LSO image. As is explained below, this may be achieved by the use of time stamps. For example, of Scn_2 may have a time stamp that may be closer to the time stamp of Img_3 or Img_4, than to the time stamp of Img_2.

This may also be achieved by use of the sequential identifiers shown in FIG. 2. For example, if one wishes to identify an LSO image that was captured at substantially the same time as a given OCT scan, one may first determine the OCT scan sequence (Scn_1 to Scn_n) to which the given OCT scan belongs (for example, Scn_1), and then identify its associated (preliminary) LSO image (e.g., Img_1), whose extracted motion information was (preliminarily) used to acquire the given OCT scan (Scn_1). One then may move forward (or backward) in sequence from the associated (preliminary) LSO image (Img_1) by a desired offset, e.g., move forward by one LSO image identifier (e.g., move from Img_1 to Img_2), and associate the given OCT scan to the LSO identified as Img_2.

Figure 3:
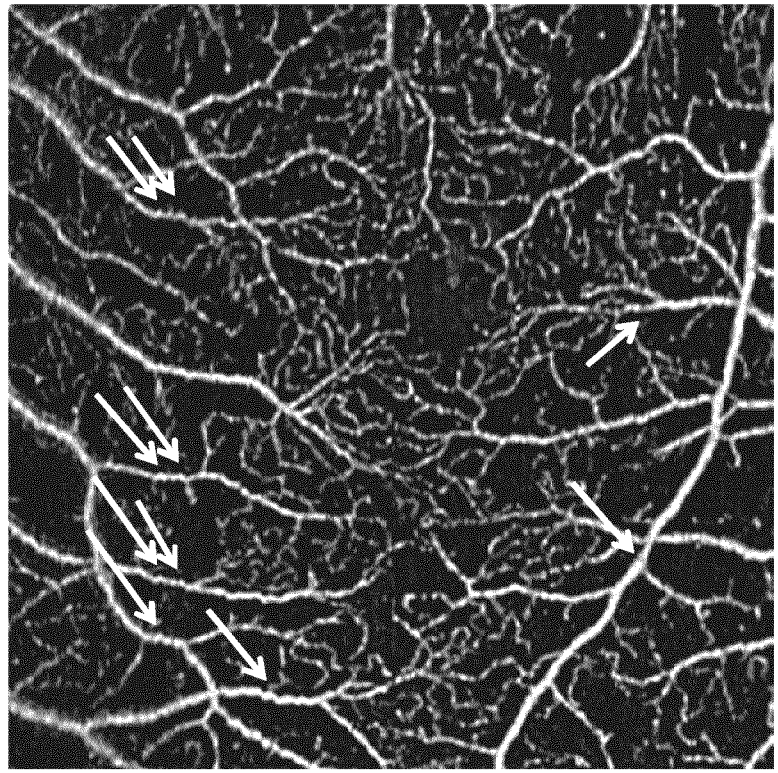
FIG. 3 illustrates an enface OCTA image (left image A) resulting from an OCT scan with typical motion correction and a corrected enface OCTA image (right image B) in accord with the present invention.
Figure 3:
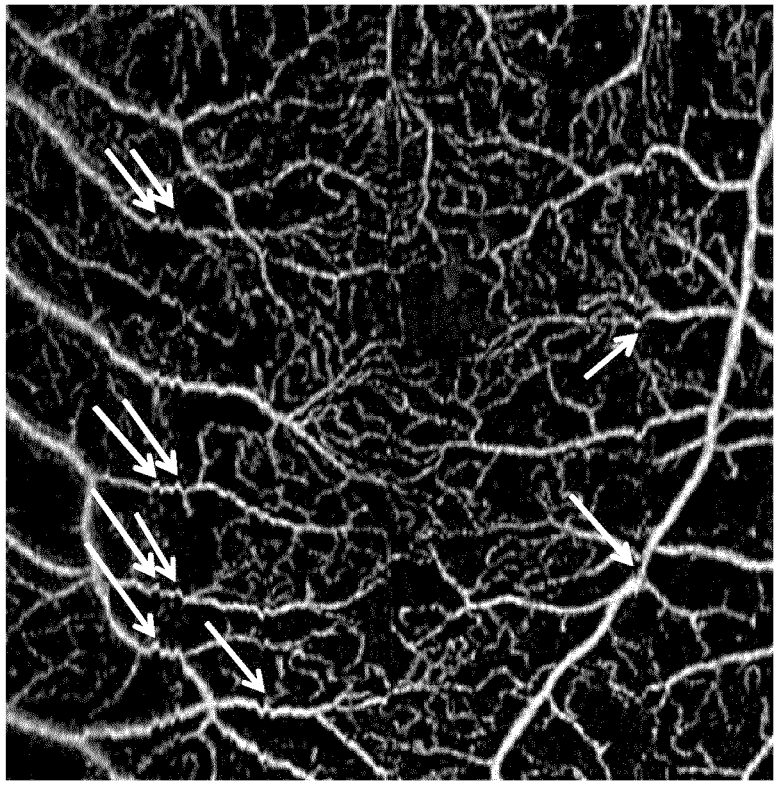

The benefits of this approach can be seen when inspecting the quality of enface OCT images, both for structure and especially in OCT Angiography (OCTA) slabs. FIG. 3 illustrates an enface OCTA image (left image A) resulting from an OCT scan with typical motion correction, as described above, and a corrected enface OCTA image (right image B) in accord with the present invention. The left image A is an example superficial OCTA slab presenting vessel jaggedness artifacts, some of which are indicated by arrows. The right image B illustrates a reduction in vessel jaggedness resulting from application of the present invention.

Although an LSO tracking algorithm may eliminate the presence of most severe vessel breaks in generated OCTA slabs, they may still produce vessel breaks of smaller magnitude and jagged vessel. These artifacts may be caused by the following four limitations. (1) The location of each acquired OCT frame (e.g., OCT scan) corresponds to the registration of an LSO image that was acquired at an earlier time (e.g., a commanded LSO image, which is the LSO image used by a tracking algorithm to guide the OCT frame acquisition) and not an observed LSO image, which is an LSO image acquired at the same time as (or closer in time to) the acquired OCT frame. Although a limited amount of movement is permissible between commanded and observed LSO images in the tracking algorithm (normally set up to be smaller than 30 microns), movement beyond this limited amount, which may occur in both X and Y axis directions, may cause vessel breaks and jaggedness in an enface image. (2) Incorrect or imprecise registration: Although a tracking algorithm may produce relatively satisfactory results, the LSO images are typically downsampled for the algorithm to be able to execute fast enough during acquisition. This fact may result in incorrect or imprecise computed transformations that are used to guide the OCT acquisition, with OCT images of typically higher resolution than the LSO images used in the tracking algorithm. These first two limitations (e.g., first two limiting factors) may arise from the fact that the transformation (e.g., motion tracking/compensation transformations) applied to the acquisition of a given OCT frame may not perfectly correspond to the actual transformation that could be measured at the time the OCT frame is acquired. This problem is difficult to solve during acquisition since the OCT scanner needs to be guided by an LSO image that has occurred earlier in time, but it can be mitigated with the post-processing step proposed herein below. (3) Possible misalignments in calibration between an LSO camera and an OCT camera: Since the OCT camera may be guided by the transformations observed from the OCT images, possible misalignments between the two may cause vessel breaks and jaggedness. (4) Distortion observed in LSO images with respect to OCT images: Since the OCT camera is guided by the transformations observed from the OCT images, differences of distortion between the two imaging systems at stable fixation locations may cause vessel breaks and jaggedness. The last two limitations of (3) and (4) could be mitigated, for example, by considering a better calibration of the system and restricting the margin of deviation from central fixation of the acquired LSO images in order to accept an OCT frame during acquisition. The present invention also has an advantage over motion correction techniques that require repeated acquisitions over the same OCT volume (either at limited positions in a first pass or at two orthogonal acquisitions) since this invention does not require the acquisition of a repeated volume, resulting in acquisition time and processing advantages.

In order to mitigate these artifacts, the present invention uses a post-processing solution, to be executed after acquisition of the tracked data. The present invention may enable and/or benefit the following applications:

Representation of OCT data free of artifacts related to the difference between transformations commanding the OCT scanner and actual transformations observed when the OCT data is acquired.

Reduction of artifacts related to inaccurate LSO registrations due to speed limits imposed on the tracking algorithm during acquisition.

Possible improvement in image quality in high definition (HD) B-scans.

Possible improvements in algorithms for OCT cube registration.

Increased repeatability and reproducibility both for the OCT and OCTA enface images and their possible quantifications (e.g., thickness maps, vessel density maps, etc).

Possible improvement in the accuracy of matching features from overlapped images, such as those intended to be montaged, and possible reduction of artifacts in a composite montage image.

Improvements in higher resolution angio enface images (for example Zoom angio with resolution better than 10 um).

Figure 4:
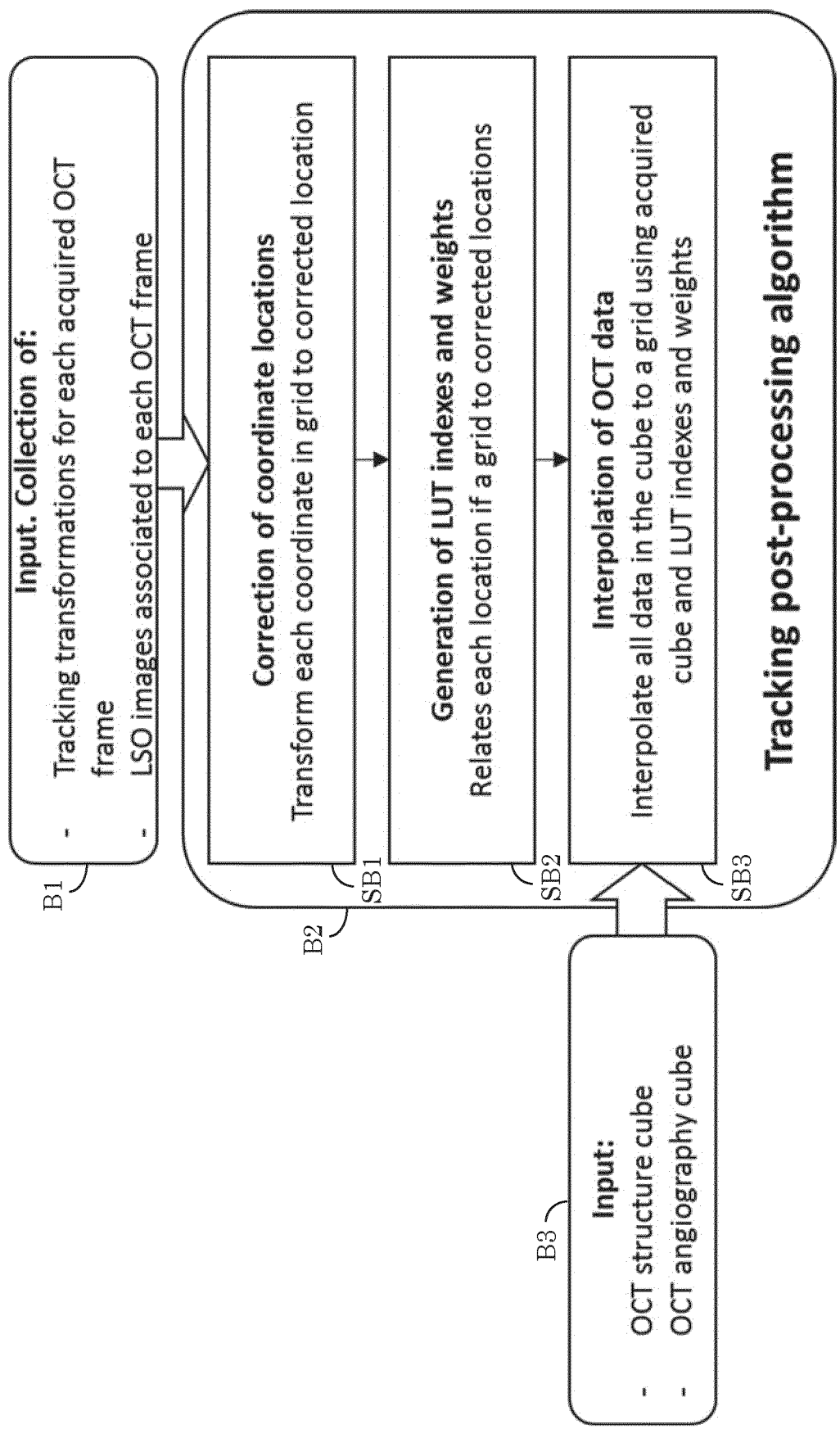
FIG. 4 illustrates some key steps in a post-processing technique in accord with the present invention.

FIG. 4 illustrates some key steps in a post-processing technique in accord with the present invention. Input block B1 receives tracking information(s) for each acquired OCT frame, and LSO image(s) associated with each OCT frame. Depending upon its intended use, the post processing technique may also receive as input an OCT structure cube and/or OCT angiography cube, e.g., block B3. Both input blocks B1 and B3 may feed into a main tracking and post-processing algorithm block B2, which may implement various features of the present invention. The main tracking post-processing algorithm block B2 may have three sub-blocks, including a Correction of Coordinate Locations sub-block SB1, a Generation of Look-Up-Table (LUT) Indexes and Weights sub-block SB2, and an Interpolation of OCT data sub-block SB3, each of which is discussed in more detail below.

Typical, OCT data (e.g. collections of B-scans) is arranged linearly and parallel to define a regular grid of A-scans, with each A-scan corresponding to a point on the grid. That is, OCT applications (e.g., algorithms or routines) may expect the OCT data to be arranged in a uniform coordinate grid, with the acquired A-scans correctly ordered within that grid. However, sub-block SB1 (Correction of Coordinate Locations) may distort this regular grid arrangement of A-scan positions in applying more closely matched motion transformations to OCT frames (e.g., applying motion transformations based on LSO images observed/determined to have been taken more closely in time to OCT frame acquisitions). That is, due to the location of each acquired OCT frame (e.g., OCT scan) received from block B1 corresponding to the registration of an LSO image that was acquired at an earlier time, and due to incorrect or imprecise registrations (see discussion on first two limitations or limiting factors, above), this expected location of each acquired OCT frame within the X-Y plane may differ from its actual, more accurate location. The goal of sub-block SB1 is to transform each expected location of coordinates in the grid to a corrected location, even if this results in an irregular point cloud of corrected locations. The inputs to perform this step are the set of tracking transformations for each acquired OCT frame and (additionally) the LSO images associated to each OCT frame, collected during tracking (from block B1). A few methods for determining the corrected, actual locations are presented here.

Since each OCT frame (e.g., OCT scan) is associated to a particular (e.g., motion) transformation $T^C$ used to command the OCT camera, e.g. guide the acquisition of an OCT scan, ($T^c=[t_x^c,t_y^c,R^c,c_x^c,c_t^c]$, with its parameters indicate the translation in X, translation in Y, rotation angle, center of rotation in X and center of rotation in Y, respectively, all computed for an LSO image with respect to a reference LSO image in a tracking algorithm), the corrections are done for each OCT frame individually. Each frame is expected to cover a set of coordinates in the fast B-scan direction ($F=[f_1, \ldots, f_i, \ldots, f_N]$) at a particular slow B-scan location ($s_j$), with N indicating the number of A-scans per fast B-scan, all coordinates in microns with respect the center of the OCT scan. These coordinates may be corrected by inverting (e.g., undoing) the effect of the original commanded transformation $T^c$ and applying the effect of an observed (i.e. matched in time) transformation $T^o=[t_x^o,t_y^o, R^o,c_x^o,c_t^o]$. This observed transformation can be considered or computed in different manners, which relates to two different post-processing scenarios, e.g., one fast and one refined, as follows:

Fast post-processing: Observed transformation $T^o$ may be taken directly from the actual transformations computed during the acquisition of OCT frames/scans, pairing each OCT frame with the transformation generated from its matched observed LSO image (e.g., the LSO image collected at the same time as, or at a time mostly closely matching, the OCT frame). This pairing helps mitigate the artifacts caused by the above-described first limitation.

Refined post-processing: Since it is likely that that the actual transformations computed during the acquisition of OCT frames/scans were based on downsampled LSO images (e.g. low resolution transformations), this approach generates new observed transformations for (e.g., each) matched LSO image. A new observed transformation T° may be computed by registering the observed (i.e. matched) LSO image in a more precise manner using the same tracking algorithm originally used (or a different algorithm if desired), but increasing the resolution of the LSO image used for tracking (for example, at full initial resolution or by upsampling the LSO image to a desired resolution), which may have been downsampled during the original OCT scan acquisition. This process further mitigates artifacts caused by the second limitation outlined in this section, e.g., imprecise registrations, but comes at the expense of increased execution time of the post-processing algorithm since new registrations need to be computed for each previously acquired OCT frame.

After an observed transformation T° is considered for a particular OCT frame, a pair of expected coordinate locations for this OCT frame may be corrected in a series of mathematical operations. These mathematical operations may be repeated for all expected coordinate locations of the same OCT frame using its associated commanded transformation T$^c$ and observed transformation T°, and repeated frame by frame considering their particular associated transformations. While the input locations ($f_i$; $s_j$) follow a grid with constant spacing defined by the separation between the collected A-scans, the corrected locations ($f_i'$, $s_j'$) may not follow such a grid, but may come in the form of a point cloud.

Figure 5:
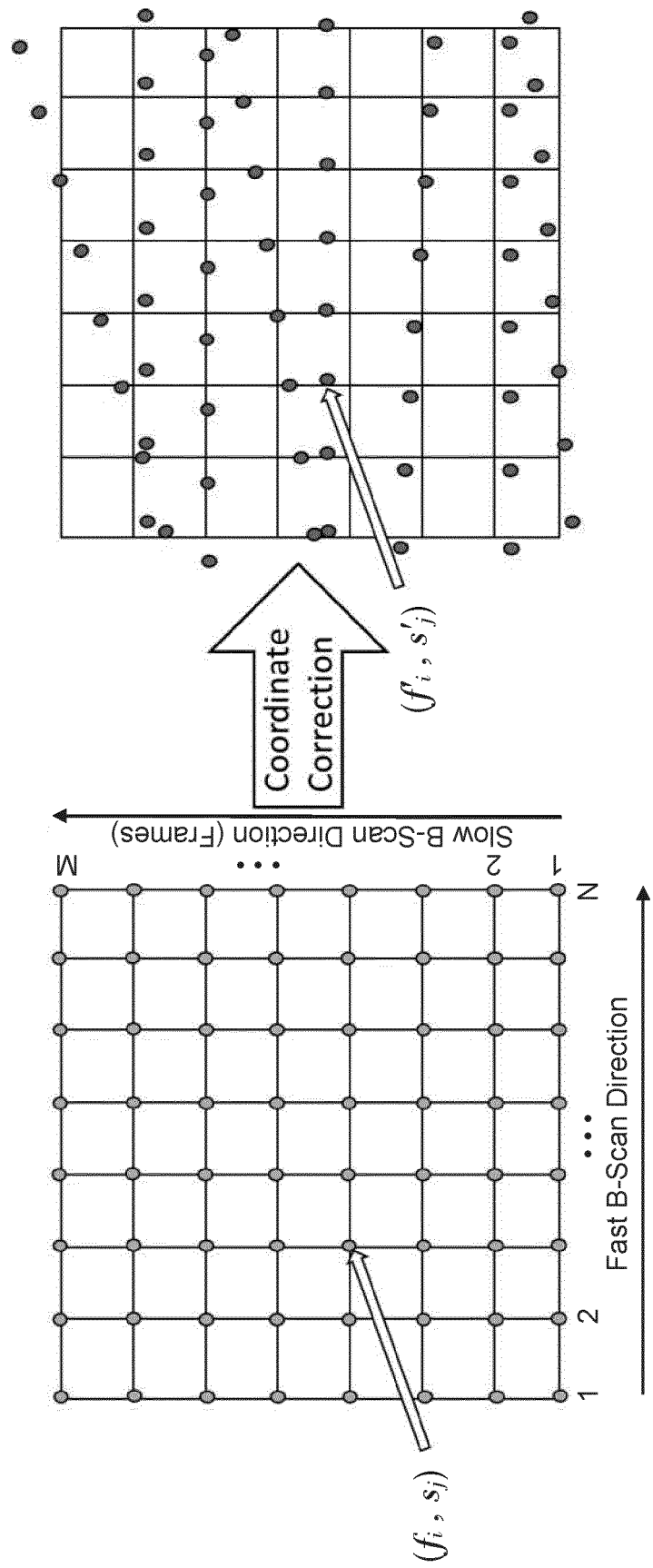
FIG. 5 provides a visual explanation the shifting of original A-scans at input locations $(f_i, s_j)$ to corrected locations $(f_i', s_j')$, which may constitute an irregular point cloud of locations.

FIG. 5 provides a visual explanation the shifting of original A-scans at input locations ($f_i$, $s_j$) to corrected locations ($f_i'$, $s_j'$), which may constitute an irregular point cloud of locations. That is, coordinate correction shifts the A-scan locations from a grid of points to a point cloud. The following is an example method of providing coordinate correction.

Since the transformations are computed from the registration of LSO images and their parameters are defined in the LSO coordinate system, the first step is to translate the locations of the OCT frame (in microns) to the LSO coordinate system. Considering the typical case where LSO acquisitions are in vertical lines and OCT acquisitions are in horizontal lines, this process typically corresponds to the following operation (although it may vary for different scan patterns):

$$LSO_x = -s_j$$

$$LSO_y = -f_i$$

Then, the effect of the commanded transformation T$^c$ may be inverted. This operation is equivalent to re-computing the location of the coordinates in the OCT frame if one assumes no transformations were passed to the OCT camera for OCT scan acquisition (e.g., tracking is turned off):

$$[LSO_x', LSO_y'] = \left(\begin{bmatrix} \cos(R^c) & -\sin(R^c) \\ \sin(R^c) & \cos(R^c) \end{bmatrix} \cdot ([LSO_x, LSO_y] - [c_x^c, c_y^c])\right) + [c_x^c, c_y^c] + [t_x^c, t_y^c]$$

The effect of the observed transformation T° may then be applied. This operation is equivalent to computing the location of the coordinates in the OCT frame if the observed transformation was passed to the OCT camera for OCT scan acquisition:

$$[LSO_x'', LSO_y''] = \left(\begin{bmatrix} \cos(R^{o-}) & -\sin(-R^o) \\ \sin(-R^o) & \cos(-R^o) \end{bmatrix} \cdot ([LSO_x', LSO_y'] - [t_x^o, t_y^o] - [c_x^o, c_y^o])\right) + [c_x^o, c_y^o]$$

The remaining step is to convert these coordinates back to the OCT coordinate system, obtaining the corrected coordinates for that location in the frame:

$$f_i' \leftarrow -LSO_y''$$

$$s_j' \leftarrow -LSO_x''$$

Once this process is repeated for each coordinate in the frame and for all the frames in the OCT cube (considering the appropriate transformations for each frame), the result is a point cloud of corrected locations for each A-scan in the cube, such as illustrated in FIG. 5.

This irregular point cloud of A-scan locations may complicate the functionality of some processes that may expect A-scans to be arranged in regular grid pattern. Therefore, there is a need to generate a regular grid pattern arrangement of A-scans from the irregular point cloud. One method of doing this is to use the point cloud of A-scans to interpolate A-scans at regular grid point locations. It has been found that the use of a look-up table (LUT) may facilitate the generation of these interpolated A-scans. Sub-block SB2 (Generation of LUT indexes and weights) addresses the generation of such a LUT.

As illustrated in FIG. 5, sub-block SB1 may result in a point cloud of A-scan locations that do not necessarily follow a rectangular grid. In order to appropriately display the OCT data in a grid arrangement, one may interpolate the values (e.g., interpolate A-scans) from the point cloud of A-scans to grid locations. This process may be done for the whole OCT structure and flow cubes (e.g. volumes). Interpolating each C-scan (e.g., a layer of adjacent B-scans) in the cubes using the point cloud data may be an extremely time consuming process. However, since each individual A-scan has a singular location in the point cloud, this step can be done much faster by generating a look-up-table (LUT) of indexes in the point cloud that correspond to a particular location in the grid, as well as a given weight for the interpolation of each index in the cloud.

This process may be accomplished by triangulating the point cloud so that each location in the point cloud corresponds to a vertex in a set of triangles. On way to generate this triangulation is by following a Delaunay triangulation process, as it is known in the art (a discussion of Delaunay triangulation may be found on website en.wikipedia.org/wiki/Delaunay_triangulation). The present example uses the OpenCV library implementation of Delaunay triangulation. OpenCV is an open source computer vision library freely available for academic and commercial purposes. More information on OpenCV may be found at website opencv.org. OpenCV provides a fast and robust implementation of Delaunay triangulation. The result is a set of triangles generated from the point cloud whose vertexes and edges can be easily navigated. This implementation also provides an interface to easily locate the resulting triangle that contains a particular arbitrary point within the point cloud. This way, by defining a rectangular grid (en face locations of the cube) where it is desired to interpolate an A-scan from the point cloud of A-scans, each location of the rectangular grid, represented as a point $p=(f_p,s_p)$, may be associated to three locations in the point cloud ($v_1^P=(f_1^{P'}, s_1^{P'})$, $v_2^P=(f_2^{P'},s_2^{P'})$ and $v_3^P=(f_3^{P'},s_3^{P'})$), the vertexes of the triangle that includes the location in the grid. The index LUT will then have an entry for each location in the grid and each entry will have three indexes to its respective point cloud locations associated in the grid:

$$LUT(p)=[v_1^P,v_2^P,v_3^P]$$

The weights for each of the three indexes associated to an entry in the LUT may be generated by considering the Barycentric coordinates of the grid location with respect to its associated triangle. As it is known in the art, the Barycentric coordinate system is a coordinate system in which the location of a point of a simplex (a triangle, tetrahedron, etc.) is specified as the center of mass, or barycenter, of usually unequal masses placed at its vertices. A fuller explanation of this process may be found in at website codeplea.com/triangular-interpolation. Thus, for the point p in the grid:

$$wLUT(p)=[w_1^P,w_2^P,w_3^P]$$

the weights may be computed as:

$$w_1^p = \frac{(s_2^{P'} - s_3^{P'})(f_p' - f_3^{P'}) + (f_3^{P'} - f_2^{P'})(s_p' - s_3^{P'})}{(s_2^{P'} - s_3^{P'})(f_1^{P'} - f_3^{P'}) + (f_3^{P'} - f_2^{P'})(s_1^{P'} - s_3^{P'})}$$

$$w_2^p = \frac{(s_3^{P'} - s_1^{P'})(f_p' - f_3^{P'}) + (f_1^{P'} - f_3^{P'})(s_p' - s_3^{P'})}{(s_2^{P'} - s_3^{P'})(f_1^{P'} - f_3^{P'}) + (f_3^{P'} - f_2^{P'})(s_1^{P'} - s_3^{P'})}$$

$$w_3^p = 1 - (w_1^p + w_2^p)$$

With the LUT thus generated by sub-block SB2, sub-block SB3 (Interpolation of OCT data) uses the LUT to interpolate A-scan values in a grid pattern. The LUT provides indexes and weights in which each table entry corresponds to a location in the grid (p) and is related to three locations in the point cloud ($v_1^P,v_2^P,v_3^P$) and their respective weights ($w_1^P,w_2^P,w_3^P$). Using the LUT, A-scan data may be interpolated from the original structure (OCT) or angiography (OCTA) cube to define a corrected cube. Each original A-scan in the original cube $A_i(z)$ is associated to a location in the point cloud $v_i$ (the corrected locations), so each interpolated A-scan in the corrected cube associated to a location p in the grid, $A_p'(Z)$ can then be constructed as:

$$A_p'(z)=(w_1^P \cdot A_{v_1^P}(z))+(w_2^P \cdot A_{v_2^P}(z))+(w_3^P \cdot A_{v_3^P}(z))$$

where $A_{v_1^P}(z)$, $A_{v_2^P}(z)$ and $A_{v_3^P}(z)$ describe the three A-scans in the original cube which locations corresponds to the three corrected coordinates indicated by the entry of the LUT for location p, $LUT(p)=[v_1^P,v_2^P,v_3^P]$.

Figure 6A:
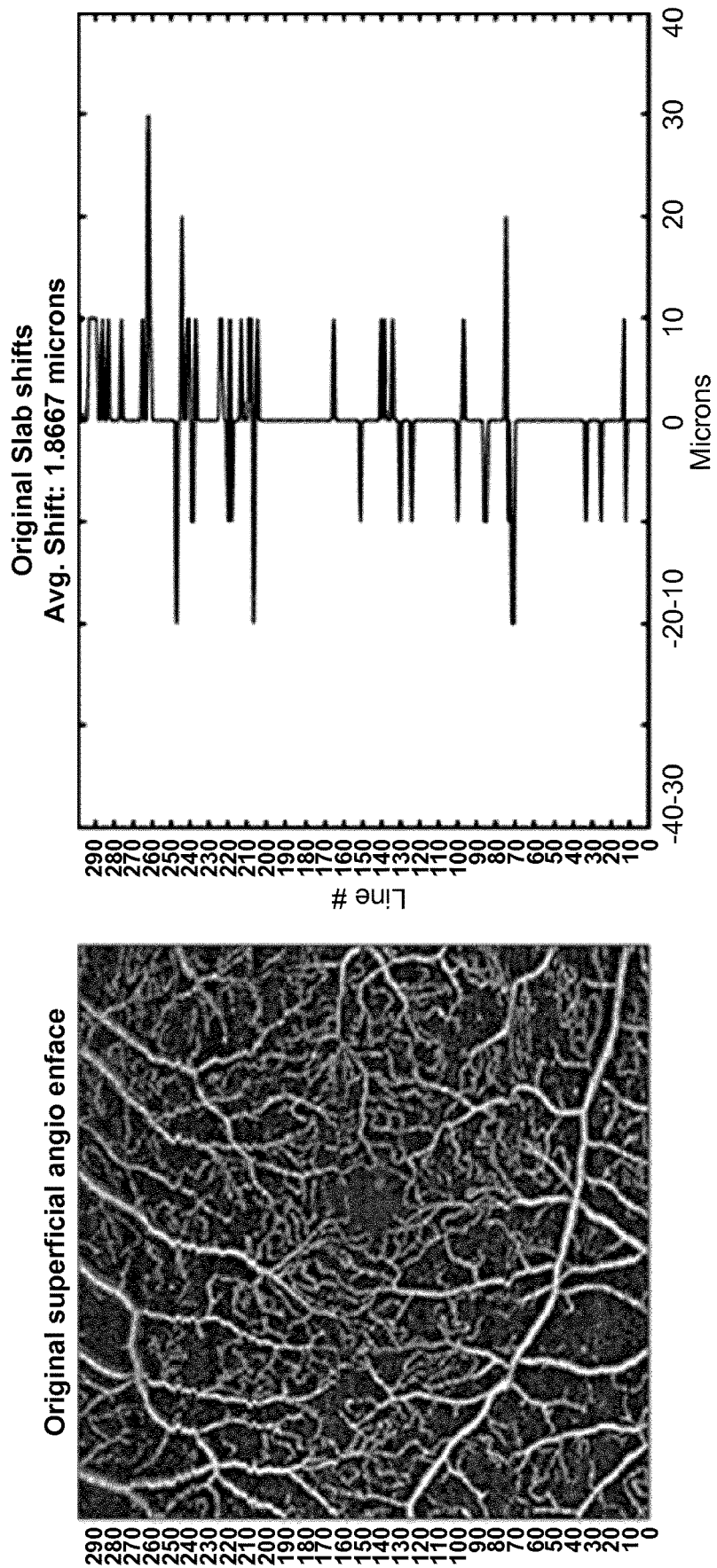
FIG. 6A displays an example case where a tracking quality metric (based on the line-by-line deviation typically seen in broken or jagged vessels) is computed before the post-processing algorithm of the present invention.

FIG. 6A displays an example case where a tracking quality metric (based on the line-by-line deviation typically seen in broken or jagged vessels) is computed before the post-processing algorithm of the present invention. Execution time and average value for the quality metric across lines is reported. As can be observed, the post-processing algorithm using the observed transformations already computed during tracking improves the jaggedness artifacts.

Figure 6B:
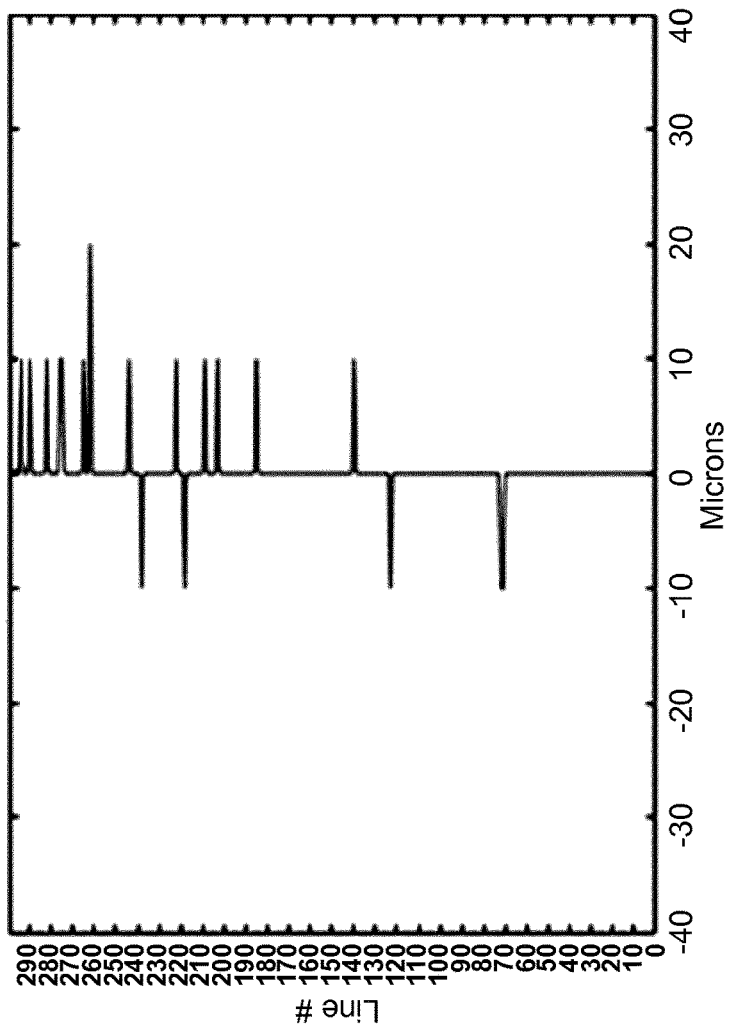
FIG. 6B displays a result after application of the fast post-processing technique to the example of FIG. 6A, in accord with the present invention, e.g., after the post-processing algorithm is executed using the observed transformations generated during acquisition.
Figure 6B:
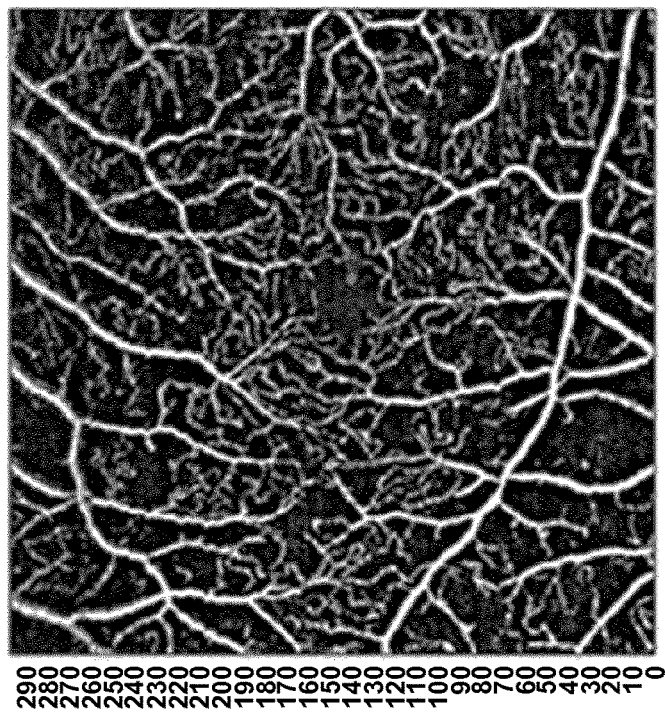

FIG. 6B displays a result after application of the fast post-processing technique to the example of FIG. 6A, in accord with the present invention, e.g., after the post-processing algorithm is executed using the observed transformations generated during acquisition.

Figure 6C:
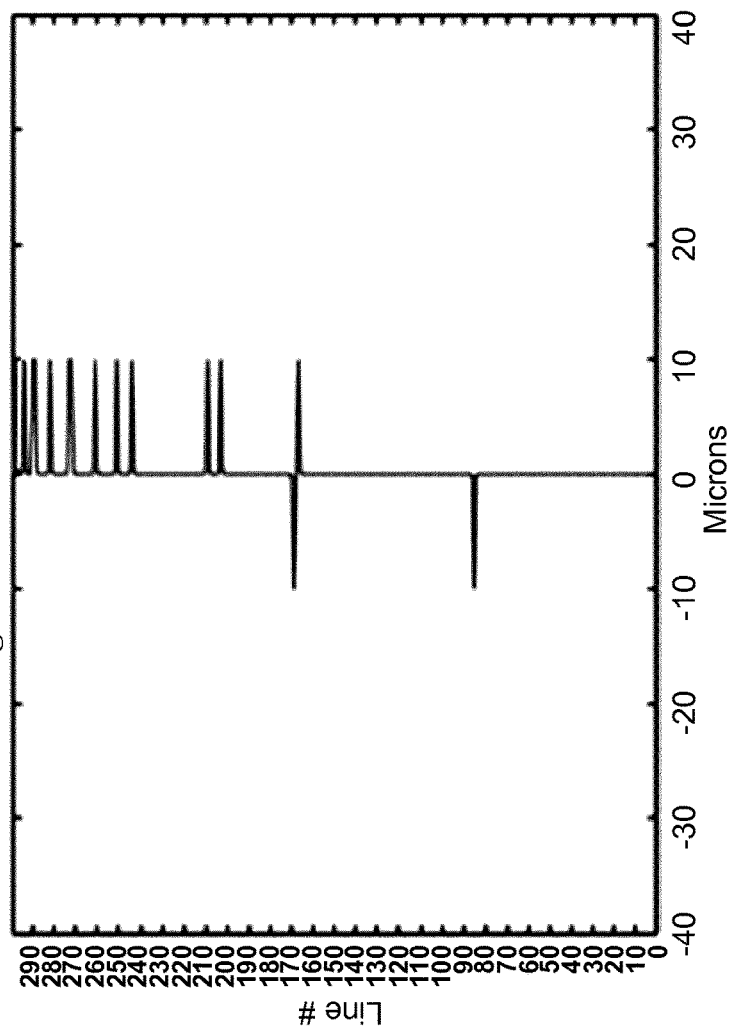
FIG. 6C displays a result after application of the refined post-processing technique to the example of FIG. 6A, in accord with the present invention, e.g., after the post-processing algorithm is executed using new registrations of the observed LSO images, or observed LSO images upsampled to the same (or of similar magnitude) resolution as the OCT images.
Figure 6C:
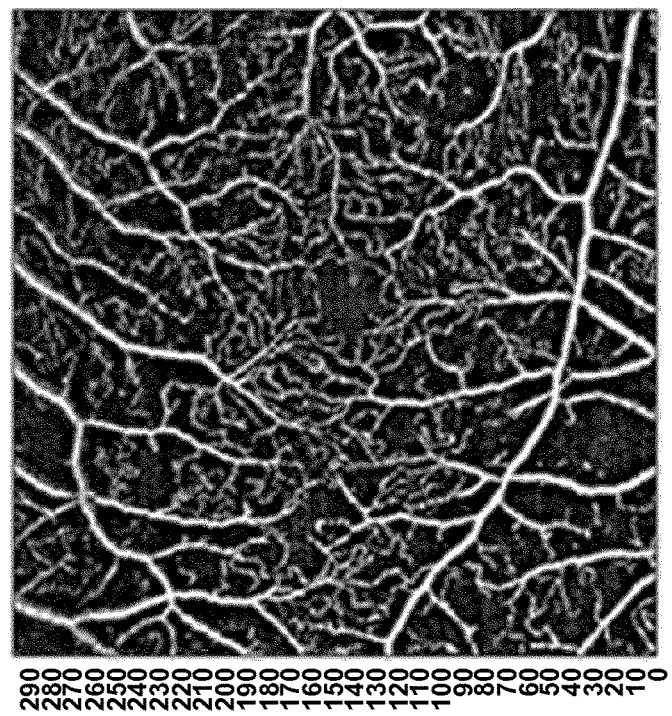

FIG. 6C displays a result after application of the refined post-processing technique to the example of FIG. 6A, in accord with the present invention, e.g., after the post-processing algorithm is executed using new registrations of the observed LSO images, or observed LSO images upsampled to the same (or of similar magnitude) resolution as the OCT images. Execution time and average value for the quality metric across lines is reported. As can be observed, the post-processing algorithm using the computation of new registrations using LSO images of higher resolution further improved the appearance of the images but at the expense of execution time (1.14 seconds vs. 61.64 seconds).

Figure 7:
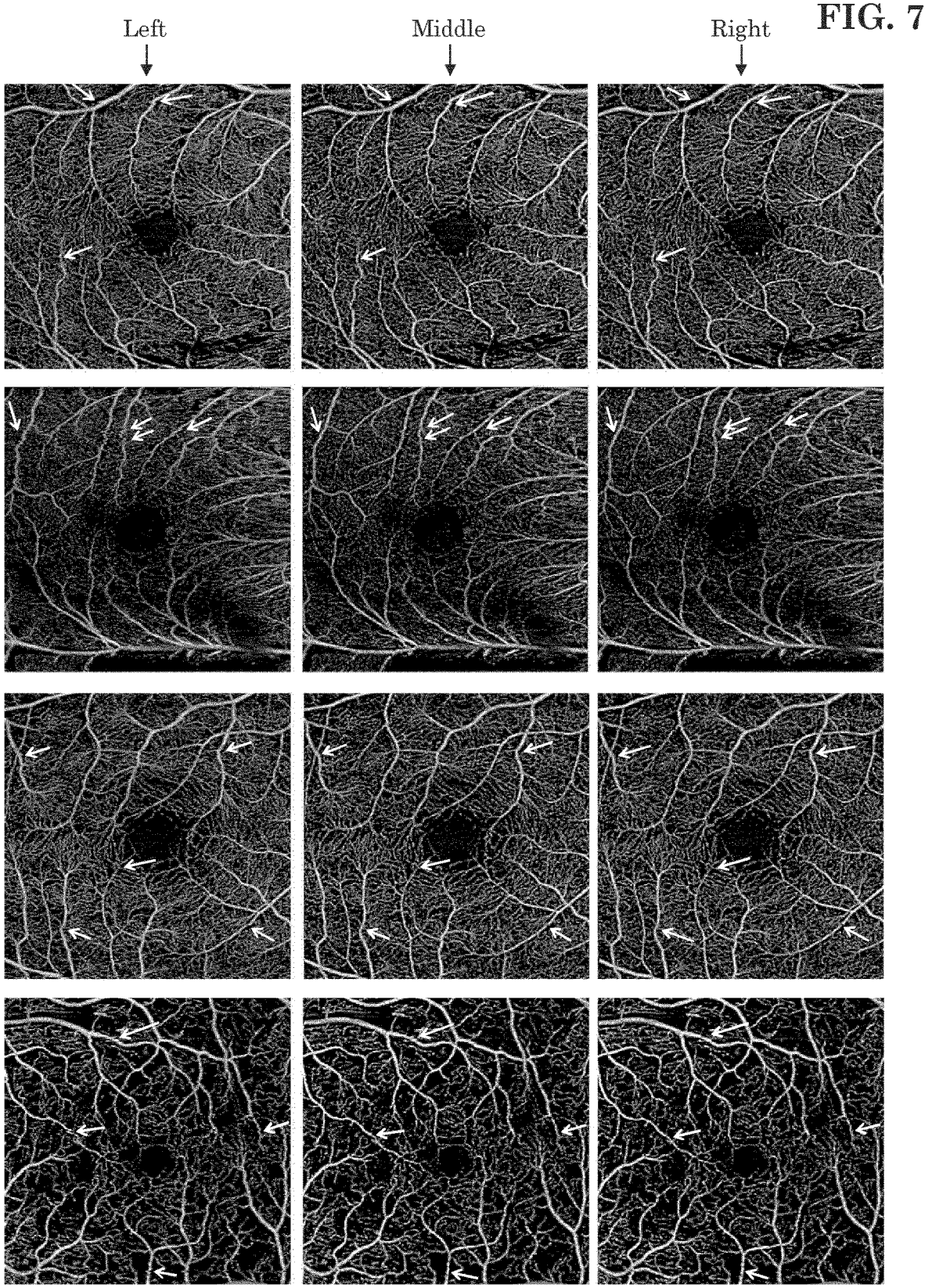
FIG. 7 displays a series of example superficial angiography slabs before, and after, application of the present fast post-processing and refined post-processing techniques.

FIG. 7 displays a series of example superficial angiography slabs before, and after, application of the present fast post-processing and refined post-processing techniques.

Each row of images results before the post-processing algorithm (left column of images), after fast post-processing (middle column of images), and after refined post-processing using new registrations of the observed LSO images upsampled to the same resolution as the OCT images (right column of images). Since differences may be subtle, the white arrows indicate some locations of artifacts in the original images (before post-processing) and their corresponding location in the post-processing results.

Figure 8:
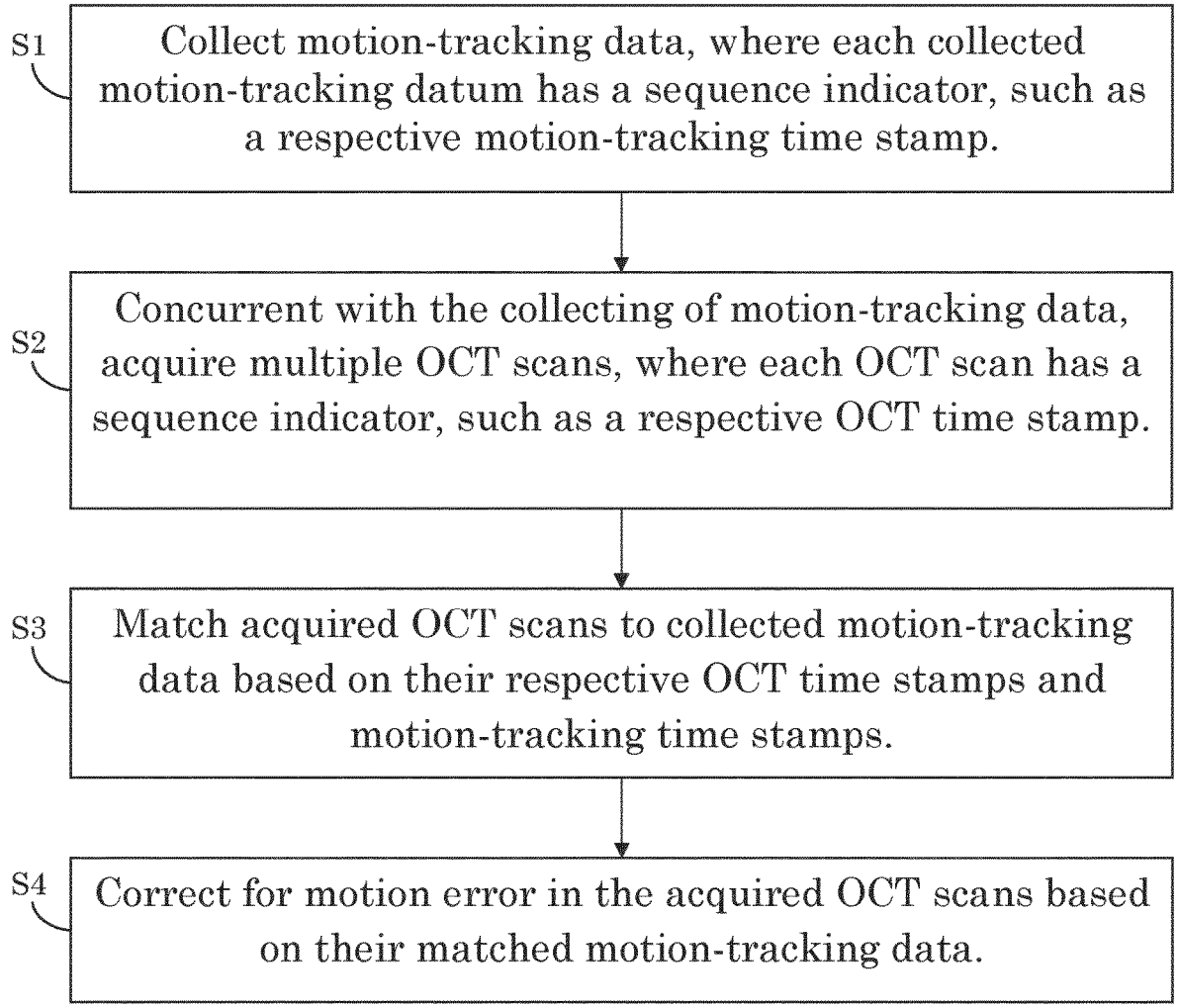
FIG. 8 illustrates an example method for motion correction in an optical coherence tomography (OCT) or OCTA system.

FIG. 8 illustrates an example method for motion correction in an optical coherence tomography (OCT) or OCTA system. Although this disclosure describes and illustrates particular steps of the method of FIG. 8 as occurring in a particular order, this disclosure contemplates any suitable steps of the method of FIG. 8 occurring in any suitable order. The method may start with collecting motion-tracking data, where each collected motion-tracking datum has a sequence indicator, such as a respective motion-tracking time stamp (step S1). In step S2, multiple OCT scans are collected concurrently with the motion-tracking data of step S1. Each OCT scan has a sequence indicator, such as a respective OCT time stamp. That is, steps S1 and S2 may be executed concurrently. As is explained above, each OCT scan may use an individual the motion-tracking datum from the motion-tracking data of step S1. That is, step S1 may collect one motion-tracking data datum after another in a sequence using an LSO and computing device. For example, as illustrated in FIGS. 1 and 2, as the LSO captures an LSO image, it is processed (e.g., compared to a reference image) to extract motion tracking information that may be encapsulated within a (motion) transformation (e.g., motion-tracking datum), which may then be passed to an OCT scanner to guide the acquisition of an OCT scan (e.g., OCT frame). Thus, the collecting of motion tracking data and OCT scans occur in parallel (e.g., concurrently). In step S3, the individually acquired OCT scans are matched to individually collected motion-tracking data based on their respective OCT time stamps and motion-tracking time stamps. As explained above, the motion-tracking datum used to guide (e.g. command) an individual OCT scan represents motion information generated before the OCT scan was acquired and may not represent true motion tracking information at the time of OCT acquisition. By matching time stamps (or other sequence indicator) to more closely match an OCT acquisition to a collected motion-tracking datum, more accurate motion tracking information may be associated/correlated to each OCT acquisition. In step S4, the already acquired OCT scans are corrected for motion error based on their matched motion-tracking information, which may not be the same as the motion-tracking information used to acquire the OCT scan. As it would be understood, this is a second motion correction step, the first being the motion correction used to acquire each OCT scan. As explained above, this motion tracking correction may include inverting (e.g., removing the effects of) the previously applied motion correction (e.g., that used at the time of OCT acquisition) and applying new motion correction, such as for example, by the fast post-processing technique and/or refined post-processing technique described above.

Figure 9:
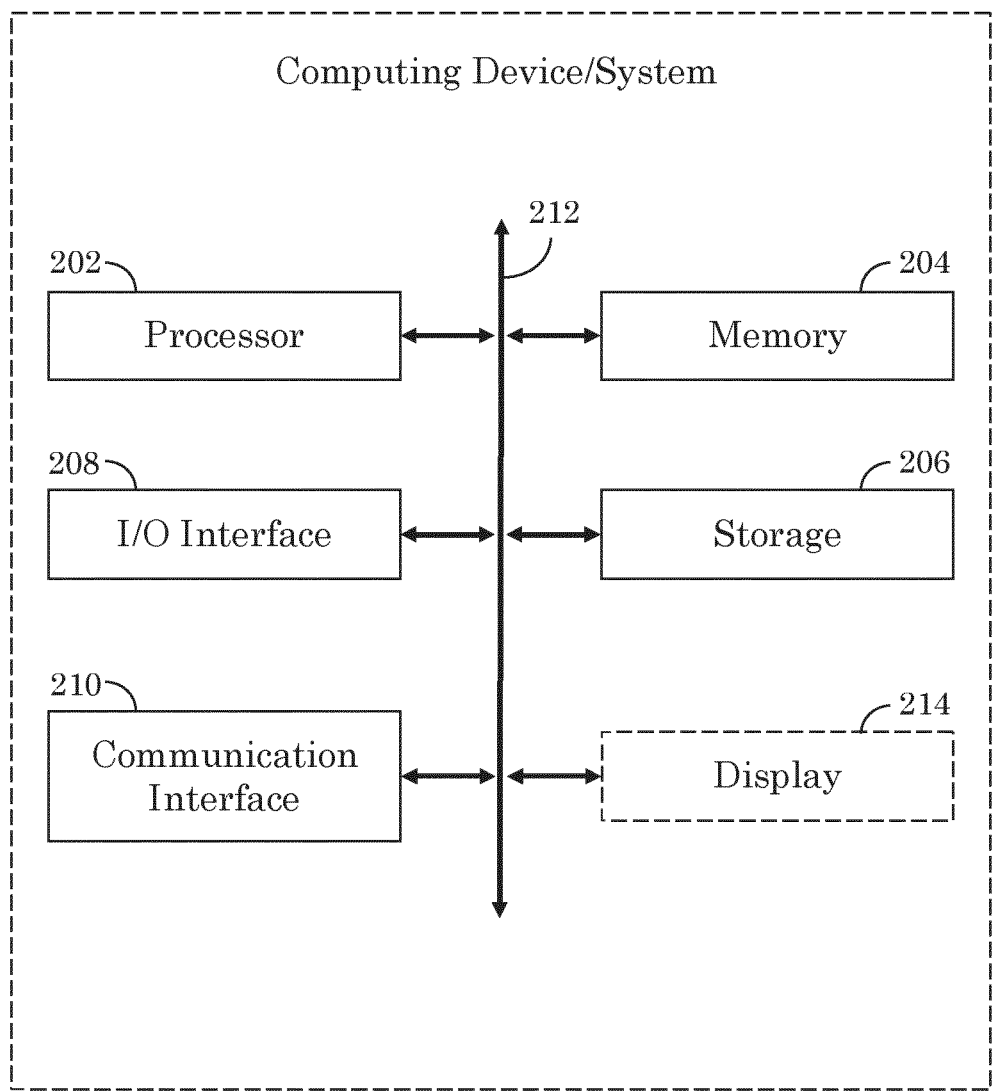
FIG. 9 illustrates an example computer device (or computer system) suitable for the present invention, e.g., for implementing an individual, or any combination of, processor 150, 153, 154, and 165 of FIG. 1.

FIG. 9 illustrates an example computer device (or computer system) suitable for the present invention, e.g., for implementing an individual, or any combination of, processor 150, 153, 154, and 165 of FIG. 1. In some embodiments, one or more computer systems may perform one or more steps of the method of FIG. 8. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, or a combination of two or more of these. Where appropriate, the computer system may reside in a cloud, which may include one or more cloud components in one or more networks.

In some embodiments, the computer system of FIG. 9 includes a processor 202, memory 204, storage 206, an input/output (I/O) interface 208, a communication interface 210, and a bus 212. The computer system may optionally also include a display 214 (e.g., display 151 of FIG. 1), such as a computer monitor or screen. Processor 202 includes hardware for executing instructions, such as those making up a computer program. For example, processor 202 may be a central processing unit (CPU) or a general-purpose computing on graphics processing unit (GPGPU). Memory 204 may include main memory for storing instructions for processor 202 to execute or to hold interim data during processing. For example, memory 204 may include random access memory (RAM), such as dynamic RAM (DRAM) or static RAM (SRAM). In some embodiments, storage 206 may include long-term or mass storage for data or instructions. For example, storage 206 may include a hard disk drive (HDD or SSD), flash memory, ROM, EPROM, or other type of non-volatile memory. I/O interface 208 may include one or more interfaces for communication with I/O devices, which may enable communication with a person (user). Communication interface 210 may provide network interfaces for communication with other systems or networks. For example, communication interface 210 may include a network interface controller (NIC) and/or a wireless NIC for communication with another computer system on a network. Communication interface 210 may further include a Bluetooth interface or other type of packet-based communication. Bus 212 may provide a communication link between the above mentioned components of the computing system.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method for motion correction in an optical coherence tomography (OCT) system, comprising:
collecting motion-tracking data associated with the eye of a patient, each collected motion-tracking datum having a respective motion-tracking sequence indicator;
concurrent with the collecting of motion-tracking data, acquiring a plurality of OCT scans of the eye, each acquired OCT scan having a respective OCT scan sequence indicator;
matching acquired OCT scans to collected motion-tracking data based on their respective OCT scan sequence indicator and motion-tracking sequence indicator; and
correcting for displacement error in the acquired OCT scans based on their matched motion-tracking data; and
storing or displaying the displacement-corrected OCT scans.

2. The method of claim 1, wherein each of the acquired OCT scans consists of a plurality of A-scan at distinct locations, and correcting for motion error in the acquired OCT scans based on their matched motion-tracking data, includes:
determining corrected locations of A-scans in the OCT scans based on their matched motion correction data, the corrected locations of A-scans constituting a point cloud of irregular point locations;
transforming the point cloud into a uniform coordinate grid with A-scans at regularly ordered positions within the grid.

3. The method of claim 2, wherein transforming the point cloud into a uniform coordinate grid includes interpolating new A-scans at the regularly ordered positions based on the A-scans at irregular point locations within the point cloud.

4. The method of claim 3, wherein interpolating a new A-scan at a regularly ordered position, includes interpolating the new A-scan based on a set of three A-scans within the point cloud whose locations define a triangle of smallest area around the regularly ordered position.

5. The method of claim 3, wherein interpolating a new A-scan at a regularly ordered position includes:
triangulating the point cloud so that each A-scan location in the point cloud corresponds to a vertex in a set of triangles;
associating each regularly ordered position within the coordinate grid to a corresponding set of three locations in the point cloud, each corresponding set of three locations defining the vertexes of a triangle that includes the associated regularly ordered position within the coordinate grid;
generating a look-up-table (LIJT) having an entry for each ordered position within the coordinate grid, where each entry includes an ordered position's corresponding set of three locations in the point cloud and weights based on Bary centric coordinates of the ordered position with respect to its associated triangle; and
interpolating the new A-scan based on the LUT.

6. The method of claim 1, wherein the motion-tracking data is comprised of a plurality of individual motion-tracking data and each individual motion-tracking datum includes an image and a first tracking transformation of first resolution based on the image, the method further comprising:
for each individual motion-tracking datum, creating a second tracking transformation of second resolution higher than the first tracking transformation; and
correcting for displacement error in the acquired OCT scans based on the respective second tracking transformation of their matched motion-tracking data.

7. The method of claim 1, wherein:
each OCT scan is associated with a corresponding motion-tracking datum, and includes application of first displacement compensation based on its associated motion-tracking datum; and
the step of correcting for displacement error in the acquired OCT scans based on their matched motion-tracking data includes:
applying second displacement compensation to the acquired OCT scans based on their respectively matched collected motion-tracking data.

8. The method of claim 7, wherein the matched collected motion tracking datum of an OCT scan is different than the associated corresponding motion-tracking datum.

9. The method of claim 7, wherein the application of first motion compensation to an OCT scan based on its associated motion-tracking datum includes using the associated motion-tracking datum to guide the acquisition of the OCT scan.

10. The method of claim 9, wherein:
each motion-tracking datum includes an image and a first tracking transformation based on the image, and each OCT scan is further associated with the image of its associated motion-tracking datum; and
the step of applying second motion compensation to the acquired OCT scans based on their respectively matched collected motion-tracking data, includes:
disassociating the image of its associated motion-tracking datum;
associating the image of its matched collected motion-tracking datum; and
generating the second motion compensation based on the image of its matched collected motion-tracking datum.

11. The method of claim 1, wherein:
each acquired OCT scan is associated with a preliminary motion-tracking datum from among the collected motion-tracking data; and
the step of matching acquired OCT scans to collected motion-tracking data based on their respective OCT scan sequence indicator and motion-tracking sequence indicator, includes:
a) for a target OCT scan whose displacement error is to be corrected, identifying the target OCT scan's associated preliminary motion-tracking datum;
b) starting from identified preliminary motion-tracking datum, shifting along the collected motion-tracking data according to their motion-tracking sequence indicators by a predefined offset to reach a target motion-tracking datum; and
c) matching the target OCT scan to the target motion-tracking datum.

12. The method of claim 11, wherein each motion-tracking sequence indicator is a motion-tracking time stamp and each OCT scan sequence indicator is an OCT scan time stamp.

13. The method of claim 12, wherein the offset is defined based on a difference between the motion-tracking time stamp of the identified preliminary motion-tracking datum and the OCT scan time stamp of the target OCT scan.

14. The method of claim 12, wherein each OCT scan is matched to the collected motion-tracking datum whose motion-tracking time stamp is closest to its OCT scan time stamp.

15. The method of claim 1, wherein the step of collecting motion-tracking data is implemented using a line scan ophthalmoscope (LSO).

16. The method of claim 1, wherein the acquired OCT scans provide OCT angiography data.

17. An optical coherence tomography (OCT) system, comprising:
a line scan ophthalmoscope (LSO) for collecting motion-tracking data, each collected motion-tracking datum having a respective motion-tracking sequence indicator;
an OCT scanner for, concurrent with the collecting of motion-tracking data, acquiring a plurality of OCT scans, each OCT scan having a respective OCT scan sequence indicator;
a data processing device for matching acquired OCT scans to collected motion-tracking data based on their respective OCT scan sequence indicators and motion-tracking sequence indicators, and for correcting for displacement error in the acquired OCT scans based on their matched motion-tracking data; and
a display for displaying the displacement-corrected OCT scans.

18. The system of claim 17, wherein each of the acquired OCT scans consists of a plurality of A-scans at distinct locations, and wherein the data processing device corrects for displacement error in the acquired OCT scans based on their matched motion-tracking data, by:
determining corrected locations of A-scans in the OCT scans based on their matched motion correction data, the corrected locations of A-scans constituting a point cloud of irregular point locations; and
transforming the point cloud into a uniform coordinate grid with A-scans at regularly ordered positions within the grid.

19. The system claim 17, wherein:
the motion-tracking data is comprised of a plurality of individual motion-tracking data and each individual motion-tracking datum includes an image and a first tracking transformation of first resolution based on the image; and
the data processing device creates, for each individual motion-tracking datum, a second tracking transformation of second resolution higher than the first tracking transformation, and corrects for motion error in the acquired OCT scans based on the respective second tracking transformation of their matched motion-tracking data.

20. The system of claim 17, wherein each motion-tracking sequence indicator is a motion-tracking time stamp and each OCT scan sequence indicator is an OCT scan time stamp, and each OCT scan is matched to the collected motion-tracking datum whose motion-tracking time stamp is closest to its scan time stamp.

21. The system of claim 17, wherein the OCT system is an OCT angiography system.

* * * * *